United States Patent [19]
Kurkov

[11] 3,933,861
[45] Jan. 20, 1976

[54] PRODUCTION OF TETRAHYDROFURANS
[75] Inventor: Victor P. Kurkov, San Rafael, Calif.
[73] Assignee: Chevron Research Company, San Francisco, Calif.
[22] Filed: Jan. 7, 1974
[21] Appl. No.: 431,258

[52] U.S. Cl. ...... 260/346.1; 252/431 R; 252/431 P; 252/429 R
[51] Int. Cl.² .................................... C07D 307/08
[58] Field of Search ............................ 260/346.1

[56] References Cited
UNITED STATES PATENTS
3,317,567   5/1967   Linn ............................ 260/346.1 R Primary Examiner—Harry I. Moatz
Attorney, Agent, or Firm—G. F. Magdeburger; John Stoner, Jr.; W. Keith Turner

[57] ABSTRACT

Tetrahydrofurans are produced by the codimerization of an alkene oxide with an alkene in the presence of catalytic amounts of a Group VIII noble transition metal compound and an iodide promoter.

11 Claims, No Drawings

PRODUCTION OF TETRAHYDROFURANS

DESCRIPTION OF THE PRIOR ART

W. J. Linn and R. E. Benson, J. Amer. Chem. Soc., 87, 3057 (1965), disclose the addition of tetracyanoethylene oxide to olefins by cleavage of the C-C bond of the epoxide ring to give tetracyanotetrahydrofurans.

SUMMARY OF THE INVENTION

It has now been found that an alkene oxide codimerizes with an alkene in the presence of a catalyst system comprising a Group VIII noble transition metal (Ru, Rh, Pd, Os, Ir, Pt) and an iodide promoter to produce tetrahydrofurans.

DESCRIPTION OF THE INVENTION

The Catalyst System

The catalyst system employed in the process of the invention comprises a Group VIII noble transition metal compound and an iodide promoter.

The transition metal compound suitably is a zerovalent to tri-valent compound. Preferably, however, the transition metal compound is low-valent, e.g., a zero-valent, mono-valent or di-valent compound. A preferred class of transition metal compounds is represented by formula (I):

$$M(L)_n(X)_m \quad (I)$$

wherein M is Ru, Rh, Pd, Os, Ir or Pt, $n$ is 0 to 5 inclusive, $m$ is 0 to 3 inclusive, the sum of $n + m$ is 3 to 6 inclusive, L is a ligand which is complexed with the metal moiety, and X is a ligand which is bonded to the metal moiety. It is appreciated, of course, that the sum of $n + m$ represents the coordination number of the transition metal compound, i.e., the transition metal compound is three-, four-, five- or six-coordinate, and that $m$ represents the valency or oxidation state of the metal moiety. It is to be understood that the transition metal compound depicted in formula (I) represents only the empirical composition of the metal compound and that the metal compound may exist in a dimeric or polymeric form.

Examples of suitable L ligands are water, carbon monoxide, olefins, organophosphines, organoarsines, organostibines, organobismuthines, and like non-ionic organic ligands which are complexed to a transition metal. Examples of suitable X ligands are halides — e.g., F, Cl, Br or I — hydride, nitrite, and like organic or inorganic anions which are bonded to a transition metal. Preferred X and L ligands are carbon monoxide, halides, and organophosphines. Particularly preferred organophosphines are trihydrocarbylphosphines of 3 to 20 carbon atoms, especially triarylphosphines such as triphenylphosphine.

Illustrative Ru compounds of formula (I) include Ru halides such as $RuCl_3$, $RuCl_3 \cdot 3H_2O$, $RuBr_3$ and $RuI_3$; Ru carbonyl halides such as $RuI_2(CO)_2$, $Ru(CO)_3Cl_2$ and $Ru(CO)_2I_3$; Ru carbonyls such as $Ru(CO)_5$ and $[Ru(CO)_4]_3$; Ru organophosphine compounds such as $Ru(CO)_2[P(CH_3)_3]_3$, $Ru(CO)_3[P(C_6H_5)_3]_2$, $RuCl_2(CO)[P(C_6H_5)_3]_3$, $RuHCl(CO)P(C_6H_5)_3$, etc.; and Ru compounds such as $RuCl_2(CO)[As(C_6H_5)_3]_3$ and $Ru(CO)_2[Sb(C_6H_5)_3]_3$.

The preferred Ru compounds are Ru carbonyl organophosphines.

Examples of Pd compounds of formula (I) include Pd halides such as $PdCl_2$ and $PdI_2$; Pd carbonyl halides such as $Pd(CO)Cl_2$ and $Pd(CO)_2Cl_2$; Pd organophosphines such as $Pd[P(C_6H_5)_3]_4$, $Pd[P(C_6H_5)_3]_3$, $PdCl_2[P(CH_3)_3]_2$, $PdI_2[P(C_6H_5)_3]_2$, and $Pd(NO_3)_2[P(CH_3)_3]_2$; and Pd compounds such as $PdCl_2[As(CH_3)_3]_2$ and $PdI_2[Sb(C_6H_5)_3]_2$.

A preferred class of Pd compounds is represented by the empirical formula (II):

$$Pd(L)_x(X)_y \quad (II)$$

wherein $x$ is 0 to 4 and $y$ is 0 to 2, the sum of $x + y$ is 2 to 4, and L and X have the same significance as defined in formula (I). As in the case of Ru compounds, the L and X ligands are preferably carbon monoxide, halides and organophosphines, as defined above. The preferred palladium compounds are zero-valent Pd organophosphine compounds.

Examples of suitable rhodium compounds include Rh halides such as $RhCl_3$, $RhBr_3$ and $RhI_3$; rhodium carbonyl halides such as $Rh_2(CO)_4Br_2$, $Rh_2(CO)_4Cl_2$ and $Rh(CO)_4I_2$; and Rh coordination compounds such as $Rh[(C_6H_5)_3P]_2(CO)I$ and $RhCl(CO)[(C_6H_5)_3As]_2$. Examples of suitable iridium, osmium and platinum compounds include $IrCl_3$, $Ir_2(CO)_4I_2$, $Os(CO)_3Cl_2$, $Pt(CO)Cl_2$, $Pt(CO)_2CL_2$, and $Pt(CO)_2Cl_4$.

The preferred transition metal compounds are Ru, Rh, Pd and Ir compounds, and the most preferred transition metal compounds are Ru and Pd compounds.

The iodide promoter component of the catalyst system suitably includes iodine, hydrogen iodide (hydroiodic acid), alkyl iodides and iodohydrins. Suitable alkyl iodides are those of 1 to 6 carbon atoms and 1 to 3 iodide groups such as methyl iodide, ethyl iodide, methylene diiodide, iodoform and isopropyl iodide. Suitable iodohydrins are vic-iodohydrins of 2 to 6 carbon atoms produced by cleavage of an alkene oxide with hydrogen iodide such as 2-iodoethanol, 2-iodopropanol, 1-iodopropan-2-ol, 2-iodobutan-1-ol, etc. The preferred iodide promoter is hydrogen iodide.

Molar ratios of the iodide promoter to the transition metal component of the catalyst system in the range of 1:1 to 2000:1 are generally suitable. However, the preferred molar ratios of iodide promoter to transition metal component are about 3:1 to 300:1, and the most preferred molar ratios are about 10:1 to 150:1.

Concentrations of the transition metal component of the catalyst system in the reaction medium between $10^{-6}$ mol/liter and $10^{-1}$ mol/liter are normally employed, with the preferred range being $10^{-3}$ mol/liter to $10^{-1}$ mol/liter. Higher concentrations, even to the extent of 1 mol/liter, may be used, however, if desired.

The concentration of the iodide promoter portion of the catalyst system in the reaction medium may vary widely over the broad concentration range of $10^{-6}$ mol/liter to 2 mols/liter, based on iodine. In the process of this invention, however, the preferred concentration range of promoter is $10^{-2}$ mol/liter to 1.5 mols/liter.

Alkene Oxide Reactant

The alkene oxide reactant has 2 to 6 carbon atoms, and is represented by the following formula (III)

(III)

where $R^1$, $R^2$, $R^3$ and $R^4$ are hydrogen or an alkyl group of 1 to 4 carbon atoms. Examples of suitable alkene oxide reactants are ethylene oxide, propylene oxide, 1-butene oxide, 2-butene oxide, 1-pentene oxide, 2-pentene oxide, 1-hexene oxide, 3-methyl-1-butene oxide and 2,3-dimethyl-2-butene oxide. Preferred alkene oxide reactants are oxides of n-alkenes, especially ethylene oxide and propylene oxide.

Alkene Reactant

The alkene reactant has 2 to 6 carbon atoms and is represented by the formula (IV)

(IV)

where $R^5$, $R^6$, $R^7$ and $R^8$ are hydrogen or an alkyl group of 1 to 4 carbon atoms. Examples of suitable alkene reactants are ethylene, propylene, 1-butene, 2-butene, isobutylene, 1-pentene, 3-methyl-1-butene and 2-hexene. Preferred alkene reactants are n-alkenes, and particularly preferred alkene reactants are terminal n-alkenes, especially ethylene and propylene.

Tetrahydrofuran Products

In terms of the alkene oxide and alkene reactants depicted by formulas (III) and (IV), the codimerization reaction may be depicted as follows:

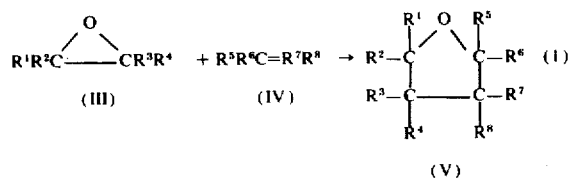

where the R groups are hydrogen or alkyl groups of 1 to 4 carbon atoms. By way of illustration, the reaction of propylene oxide and ethylene produces 2-methyltetrahydrofuran; the reaction of 2-butene oxide and ethylene produces 2,3-dimethyltetrahydrofuran; and the reaction of 2-butene oxide and 2-butene produces 2,3,4,5-tetramethyltetrahydrofuran.

The tetrahydrofuran products have utility as solvents, as they are miscible with a variety of substances such as alcohols, ketones, esters, ethers and hydrocarbons. They also dissolve polymers such as polyvinylchloride.

In addition to the tetrahydrofurans, the process of the invention also produces other products. For example, the alkene oxide is generally also isomerized and/or reduced to an alkanol or a carbonyl compound; e.g., ethylene oxide may be converted to ethanol or acetaldehyde, and propylene oxide may be converted to acetone. Also, the alkene reactant may be polymerized, e.g., ethylene may be polymerized to polyethylene.

The Reaction Conditions

In the process of the invention, the alkene:alkene oxide molar ratios are suitably from about 10:1 to 1:10. However, preferably the molar ratios of alkene:alkene oxide are from about 10:1 to 1:1.

The process of the invention is conducted in a fluid phase, i.e., either in the gaseous or liquid phase, in the presence or in the absence of an inert reaction diluent. Suitable inert, normally liquid diluents are hydrocarbons free from aliphatic unsaturation such as hexane, heptane, octane, decane, cyclohexane, benzene, toluene and xylene. Suitable normally gaseous diluents are nitrogen, hydrogen, argon, helium, methane and ethane. In some modifications of the process, a portion of the alkene reactant suitably serves as the reaction diluent, and no additional diluents are employed. When diluent is employed, up to about 10 mols per mol of alkene oxide reactant are satisfactory. The process is suitably conducted in an inert reaction environment, so that the presence of reactive materials such as oxygen and water are desirably avoided.

The process of the invention is carried out by intimately contacting the alkene oxide and alkene in the presence of the transition metal compound and iodide promoter. A variety of procedures can be employed for contacting the reaction components with the catalyst system. In one modification, the entire amounts of alkene oxide, alkene and catalyst components are charged to an autoclave or similar pressure reactor and maintained at reaction conditions for the desired reaction period. In another modification, an active catalyst system is initially preformed by contacting at elevated temperature the transition metal compound and iodide promoter in a suitable solvent and subsequently adding the remaining reaction components.

The process of the invention is conducted at moderate temperatures and pressures. Suitable reaction temperatures varying from about 100°C. to 250°C. are satisfactory, and reaction temperatures varying from about 150°C. to 200°C. are preferred. The process is conducted at or above atmospheric pressure, and pressures from about 1 atmosphere to about 200 atmospheres are satisfactory. Reactants which are normally gaseous, e.g., ethylene, ethylene oxide, etc., are conveniently employed at partial pressures of 1 psia to 2000 psia, preferably 100 psia to 1000 psia.

At the conclusion of the reaction, the product mixture is separated and the tetrahydrofuran product is recovered by conventional means, such as fractional distillation. Unreacted reaction components are suitably recycled for further use in the process.

EXAMPLES 1–12

The codimerization of ethylene oxide or propylene oxide with ethylene in the presence of Ru(CO)$_3$[P(C$_6$H$_5$)$_3$]$_2$ and an iodide promoter was conducted in a series of experiments according to the following procedure.

A rocker bomb was charged with the ruthenium compound and flushed with nitrogen. The iodide promoter, ethylene oxide and solvent were then added to the autoclave. The autoclave was sealed and pressured with ethylene and rapidly heated to reaction temperature. Each experiment was conducted with 0.5 to 1.5 mmol of the ruthenium compound, 50 to 130 mmol of iodide promoter, 0.5 mol of ethylene oxide or propylene oxide, 1.4 mol of ethylene and 1.1 mol dry, deoxygenated benzene solvent (except Run No. 2, wherein acetonitrile was employed).

After the reaction was completed, the rocker bomb was opened and the reaction mixture analyzed by gas-liquid chromatography.

The iodide promoter, reaction temperature, pressure and time, conversion of propylene oxide or ethylene oxide, mol% yield of tetrahydrofuran (THF) based on converted ethylene or propylene oxide are tabulated in Table I. In Run 1, the product is 2-methyltetrahydrofuran.

EXAMPLES 13-23

The codimerization of ethylene oxide and ethylene in the presence of a variety of transition metal compounds and hydrogen iodide promoter was conducted by a procedure similar to that employed for Examples 1-12.

Each experiment was conducted at a temperature of 150°C. with 1 to 1.5 mmol of the transition metal compound, 50 to 130 mmol of hydrogen iodide, 0.5 mol of ethylene oxide, 1.3-1.4 mol ethylene and 1.1 mol dry, deoxygenated benzene solvent.

The transition metal compound employed, reaction pressure, conversion of ethylene oxide and the mol% yield of tetrahydrofuran (THF) based on converted ethylene oxide are tabulated in Table II.

In Table II, $\phi$ represents phenyl.

TABLE I

| Run No. | Promoter | Alkene Oxide | Temp., °C. | Time, hrs. | Press., psig | Conversion, % | Yield THF, mol % |
|---|---|---|---|---|---|---|---|
| 1 | HI | Propylene oxide | 150 | 5 | 740 | 37 | 19 |
| 2 | HI | Ethylene oxide | 125 | 5 | 670 | 23 | 22 |
| 3 | HI | Ethylene oxide | 150 | 5 | 670 | 38 | 28 |
| 4 | HI | Ethylene oxide | 175 | 5 | 870 | 84 | 20 |
| 5 | HI | Ethylene oxide | 150 | 5 | 490 | 5 | 64 |
| 6 | HI | Ethylene oxide | 150 | 5 | 650 | 49 | 22 |
| 7 | HI | Ethylene oxide | 150 | 3 | 880 | 30 | 35 |
| 8 | HI | Ethylene oxide | 150 | 5 | 1400 | 45 | 31 |
| 9 | HI/I$_2$ | Ethylene oxide | 150 | 17 | 1030 | 55 | 9 |
| 10 | HI | Ethylene oxide | 150 | 3 | 550 | 14 | 49 |
| 11 | HI | Ethylene oxide | 150 | 18 | 720 | 76 | 19 |
| 12 | HOCH$_2$CH$_2$I | Ethylene oxide | 150 | 18 | 1250 | 21 | 21 |

TABLE II

| Run No. | Catalyst | Time, hrs. | Press., psig | Conversion, % | THF Yield mol % |
|---|---|---|---|---|---|
| 13 | ($\phi_3$P)$_2$(CO)$_3$Ru | 18 | 1080 | 65 | 32 |
| 14 | RuCl$_3$×H$_2$O | 18 | 1080 | 34 | 12 |
| 15 | ($\phi_3$P)$_2$RuCl$_2$ | 17 | 1000 | 87 | 5 |
| 16 | (CO)$_3$Ru($\phi_3$PCH$_2$CH$_2$P$\phi_3$) | 5 | 820 | 46 | 7 |
| 17 | [Ru(CO)$_4$]$_3$ | 18 | 880 | 58 | 7 |
| 18 | [Ru(CO)$_4$I]$_2$/$\phi_3$P | 18 | 1060 | 33 | 5 |
| 19 | Pd($\phi_3$P)$_4$ | 5 | 1100 | 13 | 30 |
| 20 | ($\phi_3$P)$_3$RhCl/$\phi_3$P | 18 | 1550 | 35 | 3 |
| 21 | ($\phi_3$P)$_2$(CO)IrCl | 18 | 850 | 64 | 4 |
| 22 | HI only | 18 | 1000 | 25 | 0 |
| 23 | ($\phi_3$P)$_2$(CO)$_3$Ru (without promoter) | 18 | 2850 | 30 | 0 |

What is claimed is

1. A process for producing tetrahydrofurans which comprises codimerizing in the gaseous or liquid phase an alkene oxide of 2 to 6 carbon atoms of the formula

with an alkene of 2 to 6 carbon atoms of the formula R$^5$R$^6$C=CR$^7$R$^8$ wherein R$^1$, R$^2$, R$^3$, R$_4$, R$^5$, R$^6$, R$^7$, and R$^8$ represent hydrogen or an alkyl group of 1 to 4 carbon atoms, in the presence of catalytic amounts of a Group VIII noble transition metal compound of the formula M(L)$_n$(X)$_m$, wherein M represents Ru, Rh, Pd, Os, Ir or Pt; $n$ is 0 to 5 inclusive; $m$ is 0 to 3 inclusive; $n+m$ is 3 to 6 inclusive; L represents non-ionic organic ligands complexed to M selected from the group consisting of water, carbon monoxide, olefin and hydrocarbyl phosphine, arsine, stibine, and bismuthine; and X represents inorganic ions bonded to M selected from the group consisting of halide, hydride and nitrite, and an iodide promoter selected from the group consisting of iodine, hydrogen iodide, alkyl iodide and iodohydrin, at a temperature from 100°C to 250°C.

2. The process of claim 1 wherein M represents Ru or Pd.

3. The process of claim 2 wherein the alkene oxide is an n-alkene oxide and the alkene is a terminal n-alkene, and the molar ratio of alkene to alkene oxide is 10:1 to 1:1.

4. The process of claim 3 wherein $m$ is 0.

5. The process of claim 3 wherein M represents Ru and L represents CO.

6. The process of claim 3 wherein the alkene oxide is ethylene oxide, the alkene is ethylene, and the ethylene is provided at an initial partial pressure of 100 psia to 1,000 psia.

7. The process of claim 3 wherein the alkene oxide is propylene oxide, the alkene is ethylene and the ethylene is provided at a partial pressure of 100 psia to 1,000 psia.

8. A process for producing tetrahydrofurans which comprises codimerizing in the gaseous or liquid phase an alkene oxide of 2 to 6 carbon atoms of the formula

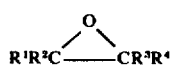

with an alkene of 2 to 6 carbon atoms of the formula R$^5$R$^6$C=CR$^7$R$^8$ wherein R$^1$, R$^2$, R$^3$, R$^4$, R$^5$, R$^6$, R$^7$, and R$^8$, represent hydrogen or an alkyl group of 1 to 4 carbon atoms, in the presence of catalytic amounts of a zero-valent ruthenium or palladium trihydrocarbylphosphine of 3 to 20 carbon atoms and an iodide promoter selected from the group consisting of iodine, hydrogen iodide, alkyl iodide, and iodohydrin, at a temperature from 100°C to 250°C.

9. A process for producing tetrahydrofurans which comprises codimerizing in the gaseous or liquid phase an alkene oxide of 2 to 6 carbon atoms of the formula

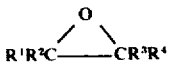

with an alkene of 2 to 6 carbon atoms of the formula $R^5R^6C=CR^7R^8$ wherein $R^1$, $R^2$, $R^3$, $R^5$, $R^6$, $R^7$, and $R^8$ represent hydrogen or an alkyl group of 1 to 4 carbon atoms, in the presence of catalytic amounts of a ruthenium or palladium carbonyl trimethylphosphine or triphenylphosphine and an iodide promoter selected from the group consisting of iodine, hydrogen iodide, alkyl iodide and iodohydrin, at a temperature from 100° to 250°C.

10. The process of claim 9 wherein the alkene oxide is ethylene oxide, the alkene is ethylene and the iodide promoter is iodine, hydrogen iodide, an alkyl iodide or an iodohydrin.

11. The process of claim 9 wherein the alkene oxide is ethylene oxide, the alkene is ethylene, and the ethylene is provided at an initial partial pressure of 100 psia to 1,000 psia, the iodide promoter is hydrogen iodide and the catalyst is $Ru(CO)_3[P(C_6H_5)_3]_2$.

* * * * *